(12) United States Patent
Liu et al.

(10) Patent No.: US 9,883,797 B1
(45) Date of Patent: *Feb. 6, 2018

(54) SYSTEM AND METHOD FOR AUTOMATICALLY TRACKING A CONTACT LENS IN A WEARER'S EYE

(71) Applicants: Gang Liu, Natick, MA (US); Lei Wang, Wayland, MA (US); Lowell D. Jacobson, Grafton, MA (US)

(72) Inventors: Gang Liu, Natick, MA (US); Lei Wang, Wayland, MA (US); Lowell D. Jacobson, Grafton, MA (US)

(73) Assignee: COGNEX CORPORATION, Natick, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/277,139

(22) Filed: May 14, 2014

Related U.S. Application Data

(63) Continuation of application No. 13/250,328, filed on Sep. 30, 2011, now Pat. No. 8,740,382.

(60) Provisional application No. 61/388,556, filed on Sep. 30, 2010.

(51) Int. Cl.
*A61B 3/14* (2006.01)
*A61B 3/10* (2006.01)
*A61B 3/00* (2006.01)
*A61B 3/113* (2006.01)

(52) U.S. Cl.
CPC .................................. *A61B 3/113* (2013.01)

(58) Field of Classification Search
CPC ........... A61B 3/113; A61B 3/103; A61B 3/14; A61B 3/125; A61B 3/1225; A61B 3/024; A61B 3/1015; G06F 3/013

USPC ....... 351/210, 200, 205–206, 209, 219, 221, 351/222, 246
See application file for complete search history.

(56) References Cited

U.S. PATENT DOCUMENTS

| | | | |
|---|---|---|---|
| 3,791,720 A | 2/1974 | Walker et al. | |
| 4,329,378 A | 5/1982 | Tarumi et al. | |
| 4,533,223 A | 8/1985 | Duparchy | |
| 4,695,399 A | 9/1987 | Neefe | |
| 4,838,679 A | 6/1989 | Billie | |
| 5,177,511 A | 1/1993 | Feuerstein et al. | |
| 6,193,373 B1 | 2/2001 | Apple et al. | |
| 6,244,707 B1 | 6/2001 | Faubl | |
| 6,334,683 B2 | 1/2002 | Apple et al. | |
| 6,445,365 B1* | 9/2002 | Taniguchi et al. ................ | 345/9 |
| 7,134,754 B2 | 11/2006 | Kerr et al. | |
| 7,258,442 B2 | 8/2007 | Noda et al. | |

(Continued)

*Primary Examiner* — Dawayne A Pinkney (57) ABSTRACT

A system and method for automated determination of position and movement of a contact lens with respect to a subject wearer's eye based upon a complimentary pair of images, acquired in rapid succession, in which one image of the pair is acquired using light that allows viewing of the pupil and/or limbus through the lens and the other image is acquired using light that is absorbed by the lens to generate an opaque image with a defined edge relative to the surrounding sclera. The images of the pair are acquired in close enough temporal proximity to ensure that eye movement in the interval therebetween is insignificant and both images are in the same approximate reference frame. Thus, the location of the pupil and limbus in one image can be accurately compared with the location of the contact lens edge in the other image.

14 Claims, 11 Drawing Sheets

(56) References Cited

U.S. PATENT DOCUMENTS

| | | | |
|---|---|---|---|
| 7,270,414 B2 | 9/2007 | Matsumura et al. | |
| 7,465,050 B2 | 12/2008 | Migliaccio et al. | |
| 7,677,645 B2 | 3/2010 | Henkelmann | |
| 7,677,730 B2 | 3/2010 | Shimizu | |
| 7,784,940 B2 | 8/2010 | Goldfain et al. | |
| 7,802,884 B2 | 9/2010 | Feldon et al. | |
| 2007/0013869 A1 | 1/2007 | Dahi et al. | |
| 2007/0177103 A1 | 8/2007 | Migliaccio et al. | |
| 2008/0212027 A1 | 9/2008 | Shimizu | |
| 2008/0246920 A1 | 10/2008 | Buczek et al. | |
| 2011/0199577 A1* | 8/2011 | Wilzbach et al. | 351/206 |
| 2011/0230751 A1* | 9/2011 | Kersting | 600/407 |
| 2014/0176900 A1* | 6/2014 | Applegate | G02C 7/027 |
| | | | 351/159.02 |

* cited by examiner

SYSTEM AND METHOD FOR AUTOMATICALLY TRACKING A CONTACT LENS IN A WEARER'S EYE

RELATED APPLICATIONS

This application is a continuation of U.S. patent application Ser. No. 13/250,328, entitled SYSTEM AND METHOD FOR AUTOMATICALLY TRACKING A CONTACT LENS IN A WEARER'S EYE, filed on Sep. 30, 2011, which claims the benefit of U.S. Provisional Application Ser. No. 61/388,556, filed Sep. 30, 2010, entitled SYSTEM AND METHOD FOR AUTOMATICALLY TRACKING A CONTACT LENS IN A WEARER'S EYE, the entire disclosures of each of which are herein incorporated by reference.

FIELD OF THE INVENTION

This invention relates to vision systems, and more particularly to vision systems used in the display and analysis of contact lens position and movement on a wearer's eye.

BACKGROUND OF THE INVENTION

For a contact lens to be effective, it should be reasonably well centered on the wearer's eye. In practice, each contact lens slides around and rotates on the surface of the eye as the observer blinks or redirects his or her direction of gaze. Therefore, the lens should be designed to quickly re-center itself after each blink and to remain reasonably well centered as the subject changes their direction of gaze. As part of the lens design process, the contact lens manufacturer conducts clinical studies of lens position dynamics. This ensures that the lens meets positional and movement requirements before it is produced and sold to end users.

Moreover, lenses are manufactured with a variety of base curvatures in order to accommodate variations in the size (corneal curvature) of individual eyes. Contact lenses are therefore "fitted" to each patient's eye. The fitting process can involve placing lenses with different base curves in the patient's eye and studying the position dynamics of the lens relative to the eye.

Prior approaches to tracking position and movement of contact lenses on a subject wearer's eye involve the use of video-capture equipment in combination with human analysts. In order to support the study of lens dynamics in research and clinical settings, one approach is to employ a color camera to acquire a video sequence of a subject wearer's eye while wearing a contact lens. A semi-automated procedure is then used to analyze the video sequence. During the semi-automated analysis, the analyzing clinician views individual frames of the video sequence on a computer display and manipulates a mouse or other user interface device to define multiple points along (1) the edge of the pupil, (2) the edge of the limbus (i.e., outer edge of the iris pattern), and (3) the edge of the contact lens. This procedure is repeated for a sampling of video frames following each eye blink. The system then fits a circle to each set of manually-entered points, and the fit circle centers for pupil, limbus, and contact lens are saved for each analyzed frame. Finally, this position data is later loaded into a spreadsheet or other formatted data file for further visualization and analysis. In particular, the offset between the center of the lens and the center of the pupil is often computed and analyzed with respect to time, as is the offset between the center of the lens and the center of the limbus.

This prior art approach typically employs broad-spectrum, visible illumination and an RGB color camera to acquire the color video sequence that is analyzed. Although the lens is transparent over the entire visible wavelength spectrum, the lens edge is generally only barely visible in the acquired images. During analysis, the most effective technique for identifying the lens edge is through human observer (typically the clinician), who can use the edge information to carefully define points on the edge of the lens. The clinician can also use these techniques to define the location of the pupil or limbus for a relative eye position. Once the edge location is manually defined, the system can then use conventional curve-fitting algorithms to fit circles to define these points. The circles allow for the generation of a center that is thereby used to track the position of the lens on the eye.

Disadvantageously, this semi-automated approach is very labor intensive and prone to human operator error. While it has the potential to significantly reduce labor and increase accuracy, the use of machine vision to locate the contact lens edge is problematic. This is because a contact lens is usually designed to be as invisible and undetectable as possible on the wearer's eye. Thus, the use of visible, broad-spectrum light does not produce an image that is reliably resolved by a vision system. An alternate approach, using machine vision, is to illuminate and image a subject wearer's eye using a contact lens that has been provided with one or more visible fiducials, along with fiducials applied to the wearer's eyelid(s) as a reference. This approach involves extra discomfort to the subject wearer as fiducials must be applied to a sensitive region. Moreover, the visible fiducials on the contact lens may cause the wearer to react differently than normal as the fiducial(s) potentially move into and out of the wearer's field of view during blink-induced lens movement.

More generally, the use of visible light to illuminate the eye during video capture is uncomfortable to the wearer. Often, relatively bright lights are needed to adequately resolve the contact lens edge. This also potentially effects the reactions of the wearer (for example, causing excessive blinking), reducing the accuracy and realism of the test results.

It is therefore desirable to provide a system and method that effectively employs a vision system to accurately and reliably track lens position and movement on a subject wearer's eye. This system and method should eliminate the need for fiducials in the determination of lens position and movement (typically on a spherical lens), and reduce or eliminate the need for bright visible-spectrum illumination and the associated discomfort it causes to the subject wearer.

SUMMARY OF THE INVENTION

This invention overcomes disadvantages of the prior art by providing a system and method for the automated determination of position and movement of a contact lens with respect to a subject wearer's eye based upon a complimentary pair of images, acquired in rapid succession, in which one image of the pair is acquired using light that allows viewing of the pupil and/or limbus through the lens and the other image is acquired using light that is absorbed by the lens to generate an opaque image with a defined edge relative to the surrounding sclera. The images of the image pair are acquired in close enough temporal proximity to ensure that eye movement in the interval therebetween is insignificant and both images are in the same approximate reference frame. Thus, the location of the pupil and limbus in one image can be accurately compared with the location of the contact lens edge in the other image. This information is used by vision system applications to determine the position of the contact lens with respect to the limbus and/or pupil in each image frame. The computed positional data from each image frame can be used to display a graphically overlaid video clip (including graphical fitted-circles and center points) of lens movement with respect to the eye and/or a variety of graphs showing decentration of the lens versus time.

In an illustrative embodiment, the system and method provides a camera constructed and arranged to acquire a first image of the eye using a first illumination at a first time in which the contact lens appears opaque with respect to the surrounding eye and a second image of the eye using a second illumination at a second time in which the contact lens appears transparent. The first time and the second time are in a direct succession with either one following the other substantially as soon as possible. This transparent image allows viewing of at least one of a pupil and a limbus of the eye. A vision system tool or process determines at least one of a location of the pupil and a location of the limbus in second image. Another vision system tool or process determines a location of the contact lens in the first image. In an embodiment, the first illumination is UV light and the second illumination is IR light.

In another embodiment a combination of IR and UV illumination can be triggered simultaneously in a single strobe and the camera can be constructed and arranged as a multi-spectral camera that images IR and UV simultaneously. Such a camera can be constructed analogously to RBG cameras which use, for example, a single sensor that includes a Bayer filter or multiple sensors that each receive transmitted light via a Prism. In such embodiments, the delay between capture of the UV and IR images is essentially zero.

BRIEF DESCRIPTION OF THE DRAWINGS

The invention description below refers to the accompanying drawings, of which.

DETAILED DESCRIPTION

Figure 1:
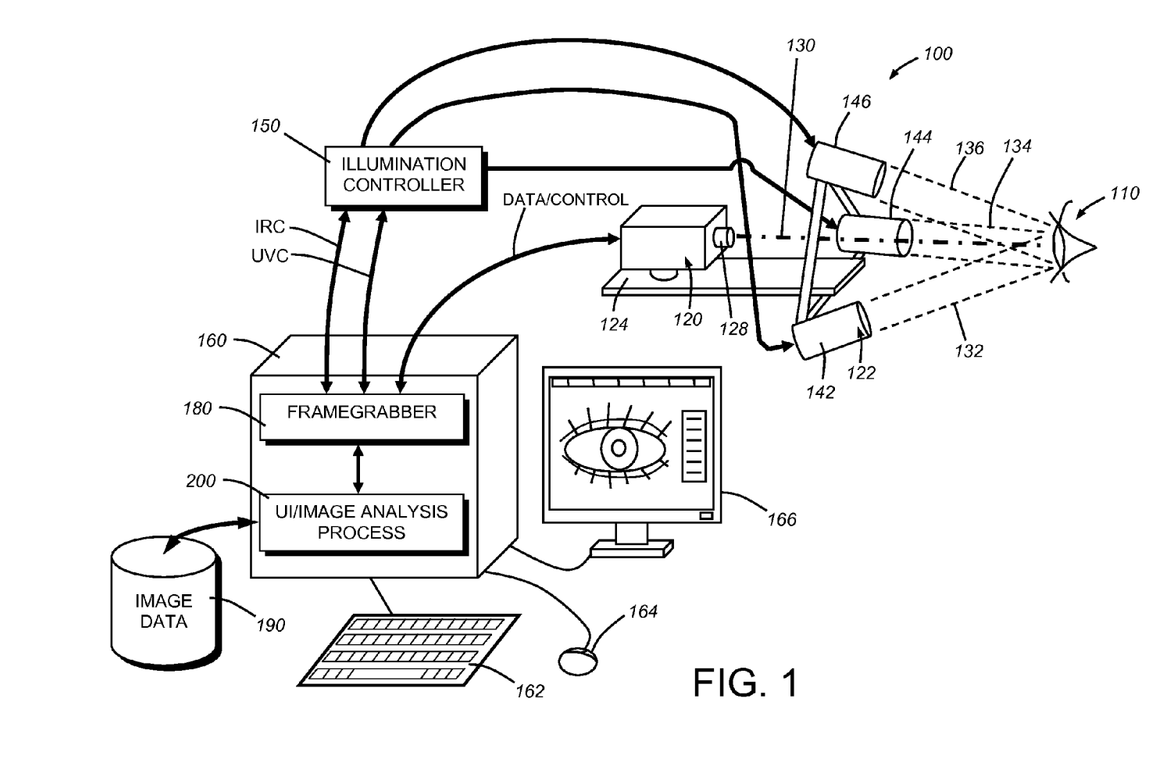
FIG. 1 is a schematic diagram of an illustrative system and method for automated tracking of contact lens position and movement according to an illustrative embodiment.

FIG. 1 details an arrangement 100 for determining and analyzing the position of a contact lens on a subject wearer's eye 110 according to an illustrative embodiment. The arrangement 100 includes a camera 120 and illumination assembly 122 that are illustratively mounted on a common framework 124. The framework or other mounting assembly for cameras and illumination is exemplary of a wide variety of possible structures that should be clear to those of ordinary skill. In general, the camera, illumination assembly and eye should be capable of variable relative positioning within a desired range of adjustability. For example the camera and illumination assembly can be mounted in a pod on an overhead gantry, while the wearer's head is secured in a conventional ophthalmologists' head brace with the wearer's chin (not shown) and forehead positioned on appropriate rests. The arrangement can be employed in a clinical study performed by, for example, researchers and/or manufacturers of contact lenses, or it can be in a practitioner's medical office for use in fitting commercially available contact lenses.

In the depicted arrangement 100, the camera 120 is aligned so that its optical axis (dashed line 130) is directed to the center of the eye 110. Each illumination beam (shown as dashed lines 132, 134 and 136) of respective illuminators 142, 144 and 146 is also directed at the eye. Notably, illuminators 142 and 144 straddle the axis 130 within a horizontal plane on opposing sides thereof, while the illuminator 146 overlies the axis 130. All three illuminators are directed at an appropriate angle to place their respective beams on the eye 110. This allows the camera to view the eye through a tunnel formed by the three surrounding illuminators.

Notably, the illuminator 146 generates a nearly invisible beam in the IR band of the spectrum. In an embodiment, the beam defines a characteristic wavelength of approximately 740-850 nm. As described below, the IR illuminator 146 can also operate in a visible light band. However, the use of relatively harmless and invisible IR allows imaging of the eye through the contact lens without the use of uncomfortable visible light. In addition, the illuminators 142, 144 operate in the UV band with a characteristic wavelength of approximately 350-370 nm. In an embodiment, the beams are generated by strobe illuminators 142, 144, 146 having spotlight geometries with appropriate optics and placement to provide a spot of approximately two inches in diameter. A larger or smaller spot can be provided to the eye region in alternate embodiments. In an operational example, which should be taken only as one possible arrangement, the illumination controller is a conventional strobe controller (240 watts, for example). In the example, each UV illuminator can be an "arealight" operating at 370 nm with ±26-degree divergence, available from StockerYale of Ireland. Likewise the IR light can be a "spotlight" operating at 740 nm with ±6-degree divergence, also available from StockerYale. In the operational example, the UV illuminators 142, 144 are spaced approximately four inches apart, the IR illuminator 146 is elevated approximately three inches above the camera axis 130, and the camera 120 is positioned approximately ten inches behind the front faces of the illuminators.

Figure 3:
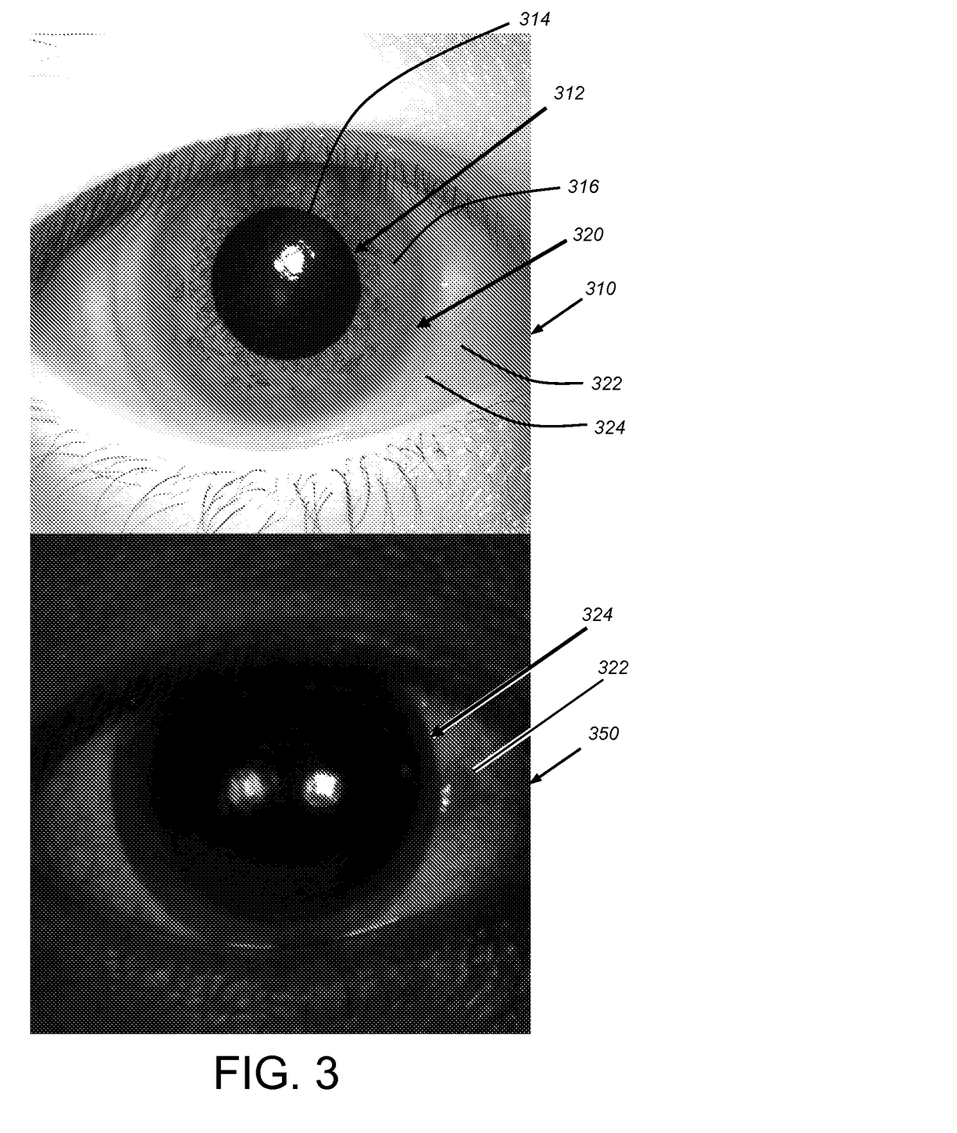
FIG. 3 is a diagram of a exemplary eye wearing a contact lens imaged for analysis using the system and method of FIG. 1, and showing the acquired images using Infrared (IR) illumination and ultraviolet (UV) illumination.

With reference to FIG. 3, the use of IR illumination (or visible light) allows the generation of an image 310 (represented as a conversion to the visible spectrum from IR) in which the boundary 312 of the pupil 314 with the iris 316 is clearly resolvable by both humans and vision system tools (due to the significant contrast at the boundary 312). Likewise, the limbus 320, which defines the boundary between the iris 316 and the mostly white sclera, is reasonably resolvable by both humans, and more notably, vision systems. However, much less clear is the edge 324 of an overlying contact lens, which extends slightly beyond the limbus.

Conversely, in the image 350 of FIG. 3 (represented as a conversion to the visible spectrum from UV), the same eye has been imaged using UV illumination, thereby defining a more-resolvable edge 324 for the contact lens relative to the sclera 322. While the sclera appears to be somewhat dark, it is still lighter around the lens edge than the very dark lens itself, affording sufficient contrast to find the edge using a vision system tool. The contact lens appears dark under UV illumination due to the inherent UV-protective characteristics provided to most contact lenses during manufacture. As such, UV light is absorbed by the lens at a significantly higher incidence than the surrounding sclera, which reflects at least some UV light. This renders the image of the lens as a dark overall spot due to its lack of UV reflection. By acquiring pairs of IR (or visible) and UV images in rapid succession, the vision system can be presented with an IR image that defines the location of the eye (pupil and limbus) and a UV image that clearly defines the location of the lens edge. Both UV and IR are nearly invisible to the subject wearer, and thus, do not cause discomfort or affect the eye's natural behavior. When the image pairs are generated with minimal latency (for example approximately 100 microseconds) therebetween, little (if any) perceived motion occurs between the lens and eye making the two images essentially complimentary views of the same point in time.

In order to generate two images in rapid succession, the arrangement 100 causes the camera 120 to first acquire one image (IR for example) while triggering the IR illuminator. This first image is buffered in the camera sensor's pixel array (analog) charge buffer, and the pixel array charge is then cleared to allow the array to quickly acquire the second (UV for example) image while the UV illumination is triggered, and after the IR is deactivated. The selective triggering of the illuminators is accomplished using an interconnected illumination controller/driver 150 that supplies power to drive the LEDs in each illuminator based upon control signals (UVC and IRC) from the computer 160. The computer can be any processing device, including a general purpose desktop or laptop PC, tablet, handheld computer, or custom data processing arrangement (also generally termed a "processor" herein). A user interface (for example, a keyboard 162, mouse, or other pointing device, such as a touch screen 164, and display 166) is interconnected with the computer 160 to allow the clinician/user to control the analysis process and handle data received therefrom.

Figure 2:
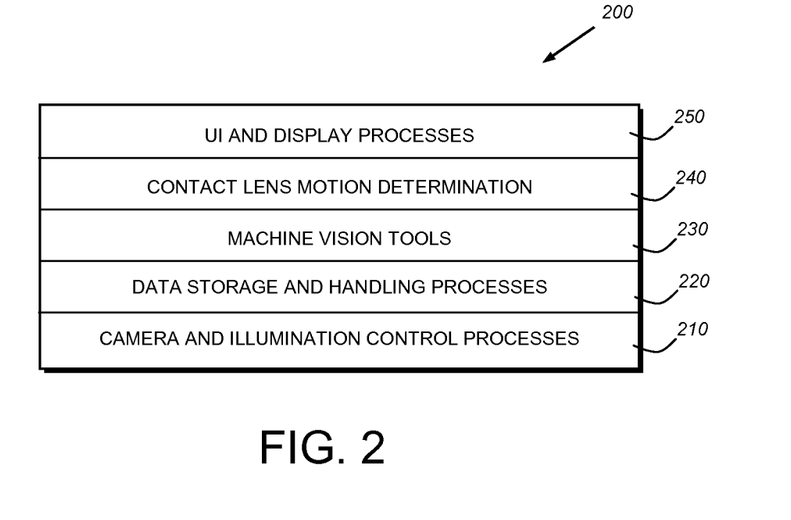
FIG. 2 is a block diagram of various hardware and/or software processes employed in the system and method of FIG. 1.

To perform the analysis, the computer/processor 160 includes a user interface (UI)/image analysis process 200, described further below, that interacts with a frame grabber hardware element 180 that interfaces with the conventional PCIe-16 port of the computer 160 (via an appropriate bus slot—not shown). The frame grabber in an illustrative embodiment is a Karbon™ four-camera unit (available from BitFlow, Inc. of Woburn, Mass.) with an interconnected control cable that issues the trigger signals to the illumination controller, and provides a DATA/CONTROL link to the camera 120. The illumination controller 150 can be any acceptable illumination driver, capable of providing appropriate power to a plurality of selected, strobed light sources, typically employing LEDs operating at a predetermined wavelength. The frame grabber 180 also provides trigger signals via the DATA/CONTROL link to the camera 120. Thus, the frame grabber 180 coordinates image acquisition and illumination triggering.

The camera 120 can be any acceptable digital camera having a sensor capable of sensing wavelengths in the IR and UV bands. One exemplary camera is the Aviator avA1000-120 km camera available from Basler AG of Germany. This camera provides a 1024×1024 pixel array with a monochromatic (grayscale) frame rate of 120 frames per seconds (fps). It is expressly contemplated that cameras from different manufacturers and with differing parameters can be employed in accordance with alternate embodiments. Notably, the frame grabber 180 employs program instructions in accordance with conventional techniques to carry out the handling of pixel array image data—thereby causing the first set of data from the IR or UV image to be buffered so that the second set of data from the UV or IR image to be acquired within the array. After the full IR/UV data set pair of a given image frame is acquired, the set is read out sequentially to the computer 160 over the DATA/CONTROL link for storage in the image data storage file(s) 190.

The camera 120 includes a fixed focal length lens 128, which in an illustrative embodiment, includes optics capable of transmitting and focusing both UV and IR light. Advantageously, this allows the same camera to image both of these illuminated views of the eye. The lens (128) in this embodiment is a Macro Apo-Componon 4.0/45 mm lens available from Schneider Optics of Hauppauge, N.Y. This lens (128) includes a front thread that is capable of accepting M37×0.75 filters. In an embodiment, band-pass filters can be provided to filter visible light in favor of the desired IR and UV bandwidths, thereby ensuring that each image includes only light of he desired wavelengths. In alternate embodiments, other lenses and filters can be employed.

It should be noted, in alternate embodiments, a plurality of discrete cameras (or sensors) and optics can be employed to image each discrete type of light—UV and IR (and/or visible). Where such an arrangement is employed, the plurality of cameras is termed a "camera" for the purposes of this description. Likewise, while one IR illuminator and two UV illuminators are shown, it is expressly contemplated that a larger number of IR illuminators positioned at appropriate locations can be employed. Likewise, a larger or smaller number of UV illuminators at appropriate locations can be employed. Moreover, the locations at which illuminators of any number are employed are highly variable, within the ambit of ordinary skill.

As described further below, the image data acquired by the computer/processor from 160 from the camera 120 is stored in the image data storage file(s) 190. This data is subsequently analyzed for lens location and movement information using the UI/image analysis process 200. The various sub-processes of the overall process 170 are depicted in overview in FIG. 2. Generally, the process 200 includes a camera and illumination control process 210 that operates the frame grabber 180 to provide instructions for triggering and data handling to the illumination control 150 and the camera 120. Data storage and handling processes 220 allow image and other data to be moved from the camera to the storage location 180, and back to the computer/processor 160 for further analysis and re-storage in a modified form.

Machine vision (and/or vision system) tools 230 are a series of conventional and/or customized processes that allow image data to be analyzed. For example, the machine vision tools can include a commercially available set of tools, such as the rotation and scale invariant search (RSIS) application, Patmax™ available from Cognex Corporation of Natick, Mass., as well as other tools including edge detection tools, blob analysis tools, caliper tools and the like—all of which should be clear to those of ordinary skill. These tools provide results based upon particular vision system tasks that can be based upon trained images or upon untrained, observed image data. Where images are trained, the user can provide an actual model image that the tool thereafter uses, or a set of synthetic image parameters, which the tool compares to an observed set of image data to decide whether the observed data matches the trained results with sufficient confidence to return a positive result. RSIS applications, such as Patmax advantageously allow an observed image to display skew with respect to a trained model so that a positive result can be returned even if the observed image does not literally match the trained model. Thus, where an eye is imaged at an angle that renders the pupil, iris and/or lens edge as an oval rather than a circle (due to off-angle orientation of the eye relative to the camera axis), the system can still operate to determine position of the contact lens with respect thereto.

The overall UI/image analysis process 200 also includes a contact lens motion determination process 240. This process 240 obtains the results from the machine vision tools and any stored data, and translates it into a series of meaningful outputs that the user can review as a display. This process can include curve and graph generation functions as well as curve-smoothing processes. This process can also include image projection processes that provide a visible version of each frame of the acquired image of the eye and contact lens, typically combining the IR image with the UV image and desired graphics (for example graphics of circles fitted to the pupil, limbus and lens edge, as well as center points for each circle). The process 240 also translates the acquired image frames into a time base, so that each frame corresponds to a particular time value (in fractions of seconds, for example) in which the frame was acquired. Note that, in an embodiment, 30 seconds worth of frames are acquired. The image pairs are acquired at a rate of 50 Hz, resulting in approximately 1500 IR/UV frame pairs. A longer or shorter duration is expressly contemplated, as is a faster or slower frame rate. It is, of course, desirable that overall duration of image acquisition be sufficiently short so that there is no potential for harmful UV radiation exposure by the subject wearer's eye.

Data stored and subsequently generated via processes 240 can populate a comma-separated file (such as a conventional Microsoft Excel® spreadsheet) for use in subsequent analysis tasks.

The generated graphs, time values and images delivered from the process 240 are visually displayed to the user using the UI and display processes 250 that can be employed according to conventional techniques. This process 250 provides viewing windows for graphics and images, as well as control buttons for acquisition, training and manipulation of acquired data—as described further below.

Note that the term "process" and/or "processes" refers both to a method for performing one or more functions of the system and method, and also to a structural hardware and/or software element, which comprises a structure that performs the particular function or functions.

Figure 4:
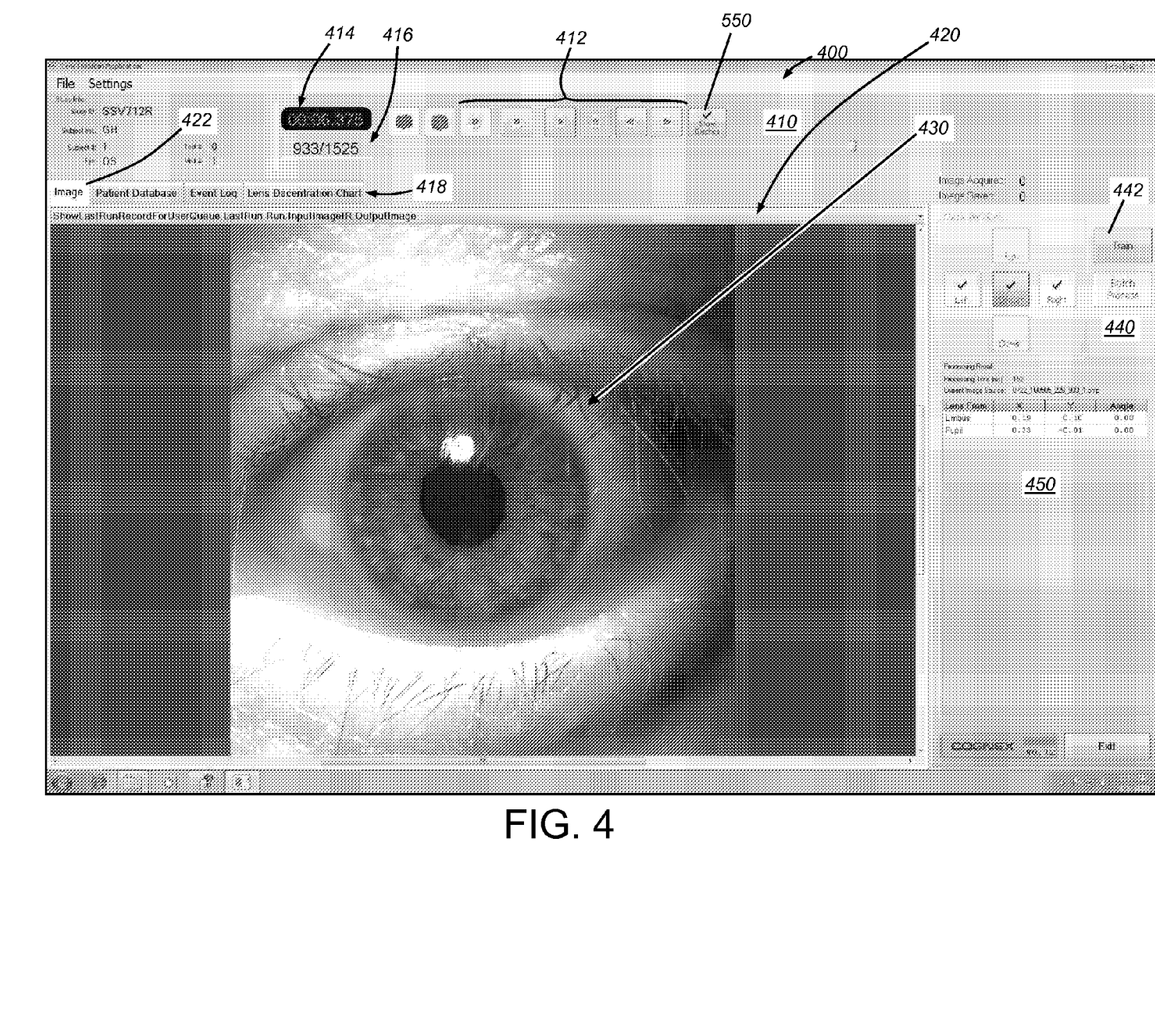
FIG. 4 is a diagram of a graphical user interface display for use with the system of FIG. 1, showing an imaged eye with contact lens.

With reference now to FIG. 4, an illustrative graphical user interface (GUI) display 400 for use with the system and method of this invention is shown. This display can be provided on the attached display monitor 166, or another display device (e.g. a handheld device screen, a laptop computer screen, or other remote monitor). The layout and functions presented on the display are highly variable. In this exemplary embodiment, the display includes a window 410 with conventional buttons 412 for controlling video recording and playback of acquired video frames of the imaged eye. A time indicator 414 shows the relative time of a given image frame or other reported data in the overall recording/playback file. The current frame number being displayed versus the total number of acquired/recorded frames (416) in the image file is also provided. A set of tabs 418 allows the user to select the particular information in the main window 420. In the depicted example, the "image" tab 422 is selected, showing a visible version of the IR image of the subject wearer's eye 430. The contact lens is barely visible. Also shown is a window 440 that allows control of the relative gaze of the wearer (i.e. is the gaze centered or biased left, right, up or down (as shown by respective buttons arranged in a cruciform pattern). In addition, there is an optional button 442 to allow training of the wearer's eye—for example to derive the relative size and position of the pupil and limbus in advance of tracking the contact lens. Additionally, there is a data window 450 that reports the relative position of the lens in the given frame along the horizontal (X) and vertical (Y) directions with respect to the limbus and pupil.

Figure 5:
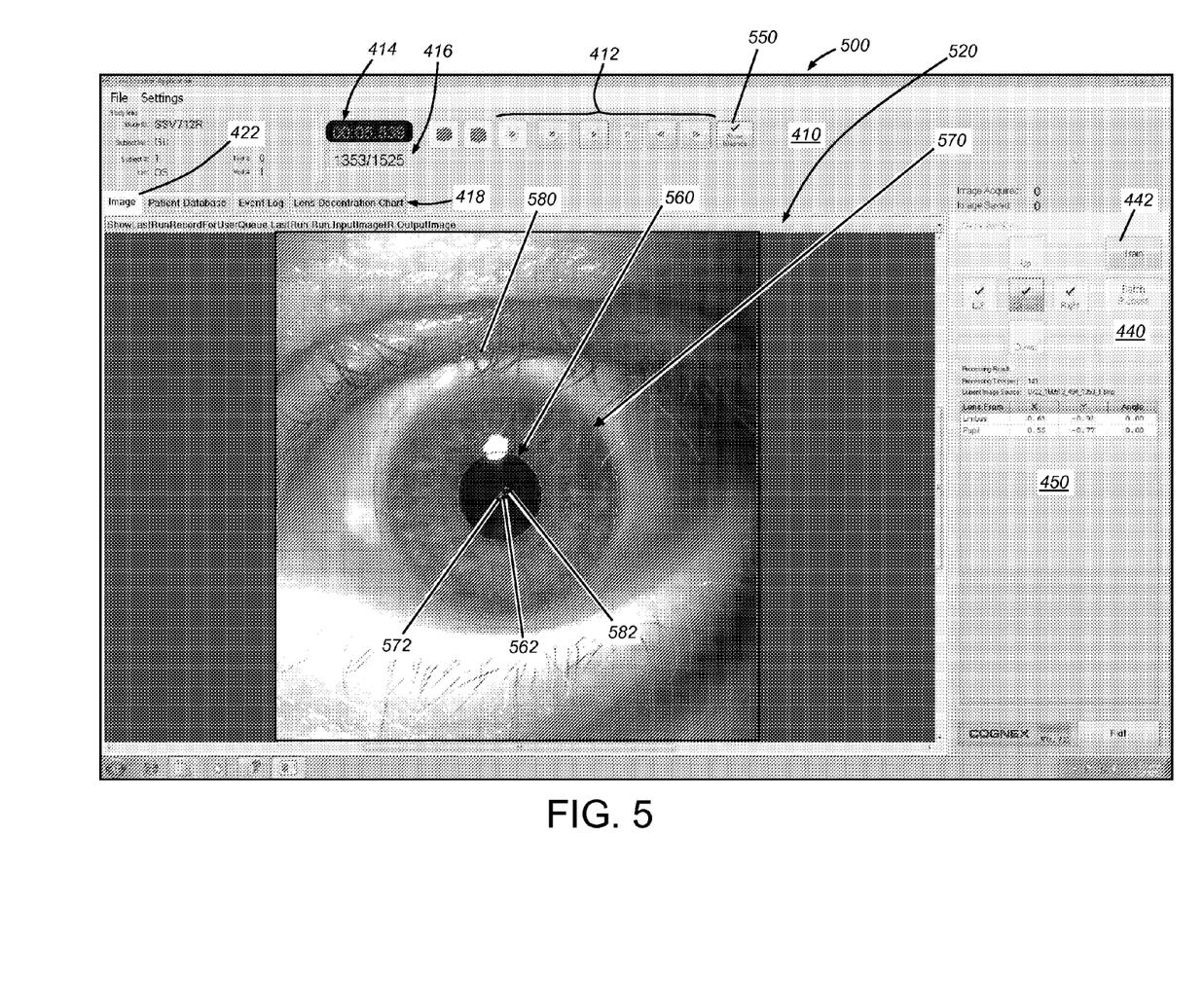
FIG. 5 is a diagram of the graphical user interface display of FIG. 4, showing the imaged eye with contact lens, and having respective circles and centers defined around the pupil, limbus and lens edge to show one relative lens position at a particular time.

With reference to FIG. 5, the GUI display 500 described generally above with respect to FIG. 4 is shown in association with another image frame (in this example frame 1353 of 1525). The displayed image 520 shows the eye with graphics (graphical overlays) included (based upon activation of button 550). These graphics comprise fitted circles of predetermined, discrete colors and/or patterns, in which the innermost, smallest-radius circle 560 comprises an approximation of the pupil diameter and position, the middle-radius circle 570 comprises the approximate diameter and position of the limbus, and the outermost, largest-radius circle 580 compromises the system-determined edge of the contact lens. Each circle 560, 570, 580 includes a respective center point in a similar color and/or pattern as the center 562, 572, 582. In this example, the lens has decentered with respect to the eye to the upper right in the image.

Figure 6:
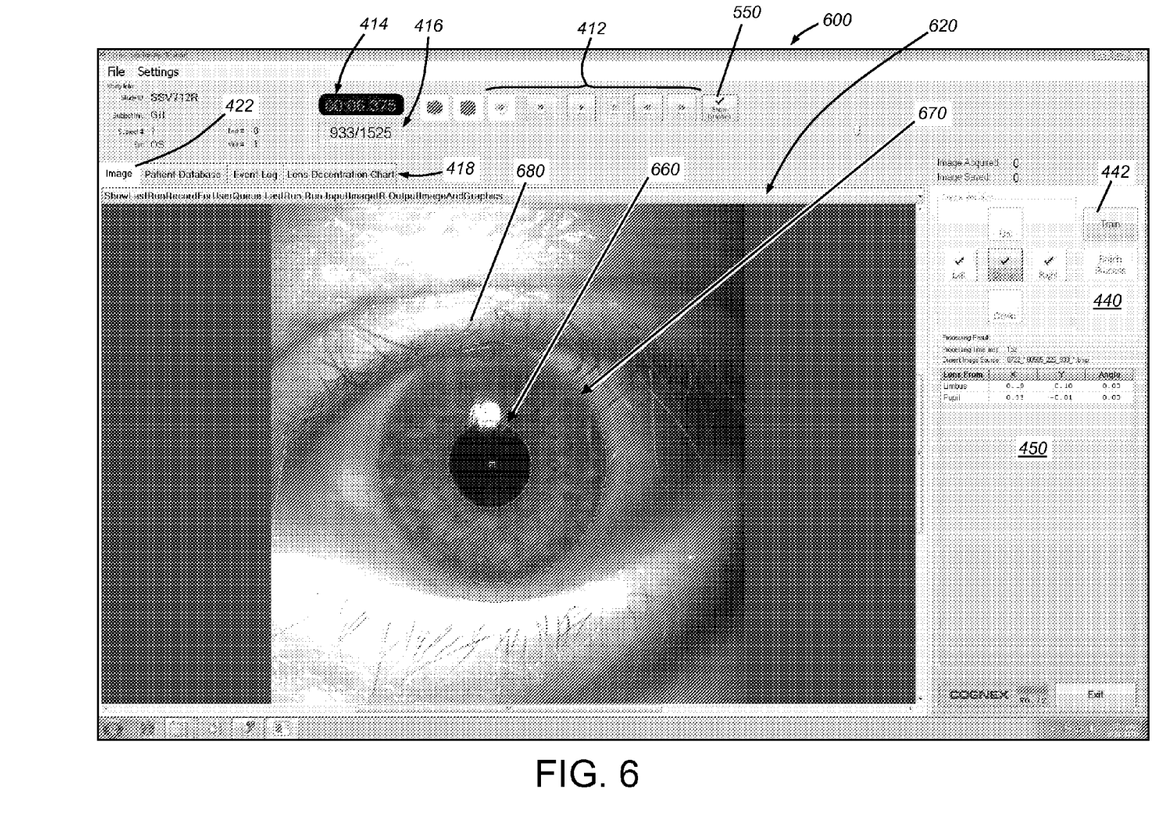
FIG. 6 is a diagram of the graphical user interface display of FIG. 4, showing the imaged eye with contact lens, and having respective circles and centers defined around the pupil, limbus and lens edge to show another relative lens position at another time.

In another depicted, exemplary image frame (933/1525) 600, the pupil, limbus and lens edge circles 660, 670 and

Figure 7:
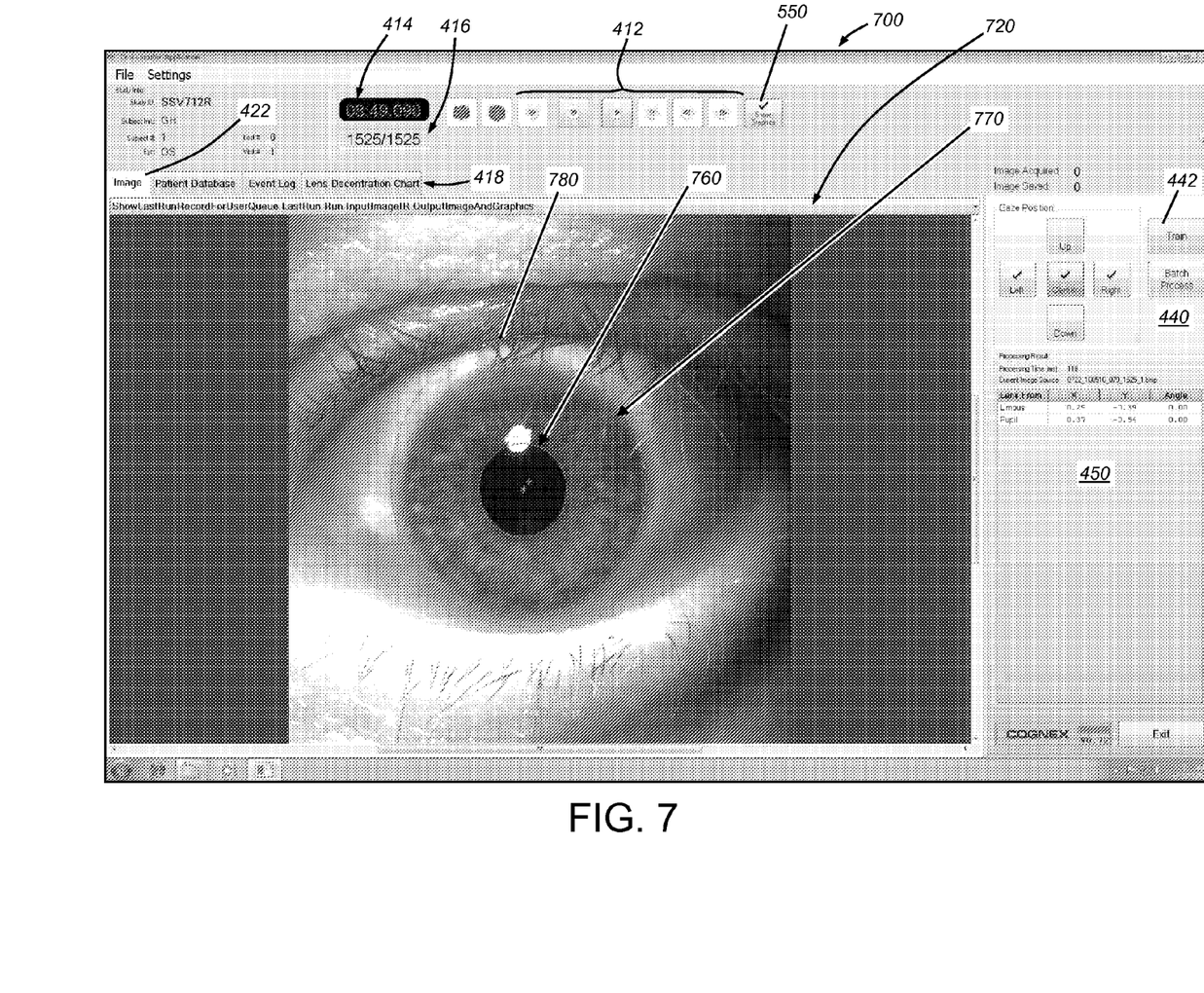
FIG. 7 is a diagram of the graphical user interface display of FIG. 4, showing the imaged eye with contact lens, and having respective circles and centers defined around the pupil, limbus and lens edge to show yet another relative lens position at yet another time.

680, respectively, are relatively concentric, as indicated by their closely adjacent center points. Finally, in the image frame 700 of FIG. 7, the lens has decentered slightly with respect to the pupil and limbus as shown by circles 760, 770, 780 and associated center points. Each frame can be depicted graphically as shown in FIGS. 5-7 by determining the relative position of the lens edge versus the eye. The procedure for determining eye position and lens position is described in further detail below.

Figure 8:
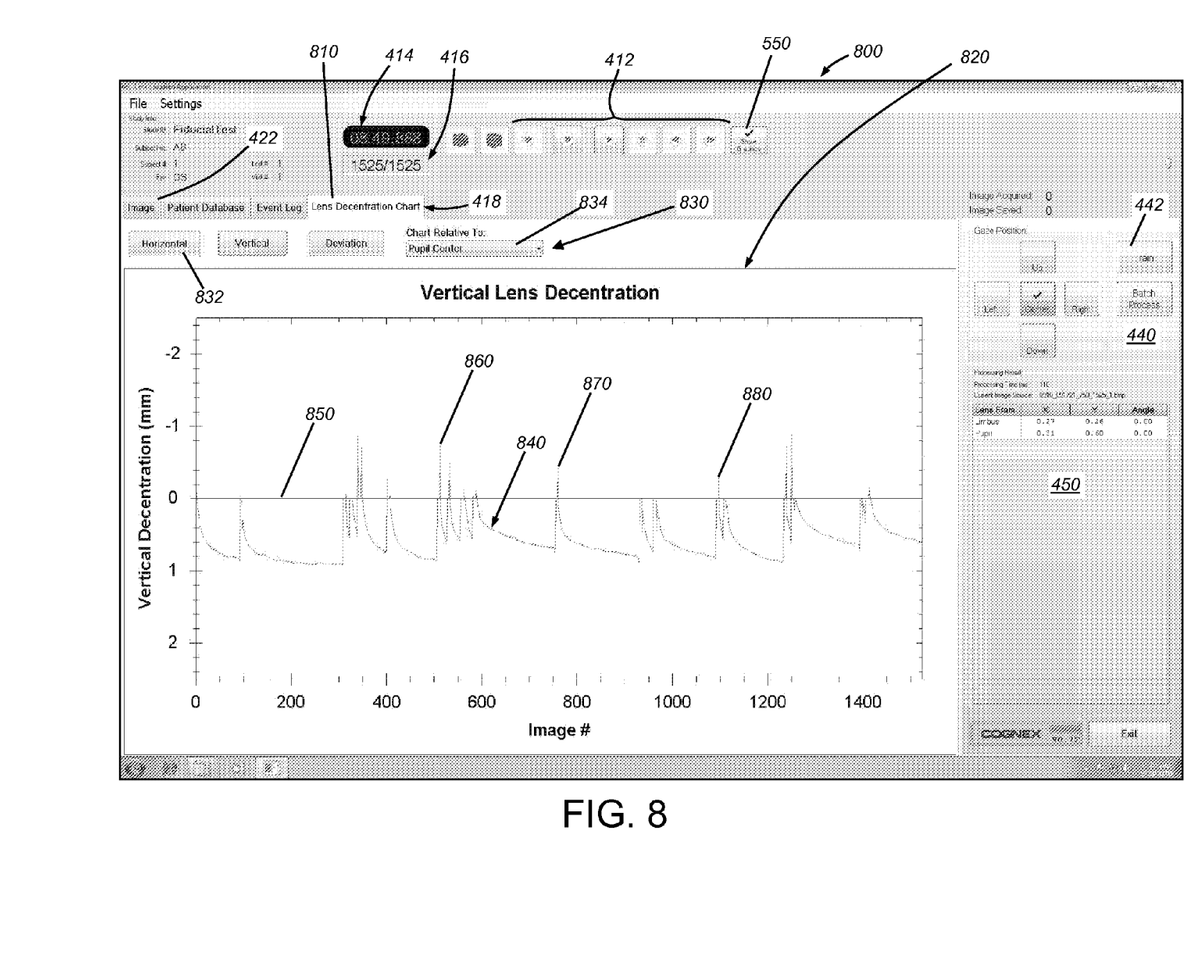
FIG. 8 is a diagram of the graphical user interface display of FIG. 4 showing a generated graph of a vertical lens decentration (vertical component of movement from a centered position on the eye) based upon a predetermined number of successive images.

With further reference to the GUI display, an exemplary display 800, shown in FIG. 8 operates using the tab "Lens Decentration Chart" 810 to display a graph 820, based upon the selected button from the window 830. In this example the vertical lens decentration has been selected via button 932. The graph 820 includes a plot 840 of vertical lens position versus the pupil center (line 850) for each image frame in the video file. A selection window 834 allows the user to decide which item that lens position is compared to—for example the pupil center or the limbus center. It should be noted that the depicted spikes, such as spikes 860, 870 and 880 represent blinks of the eye. The occurrence of blinks can be use to determine the rapidity with which the lens recenters, among other useful information.

Figure 9:
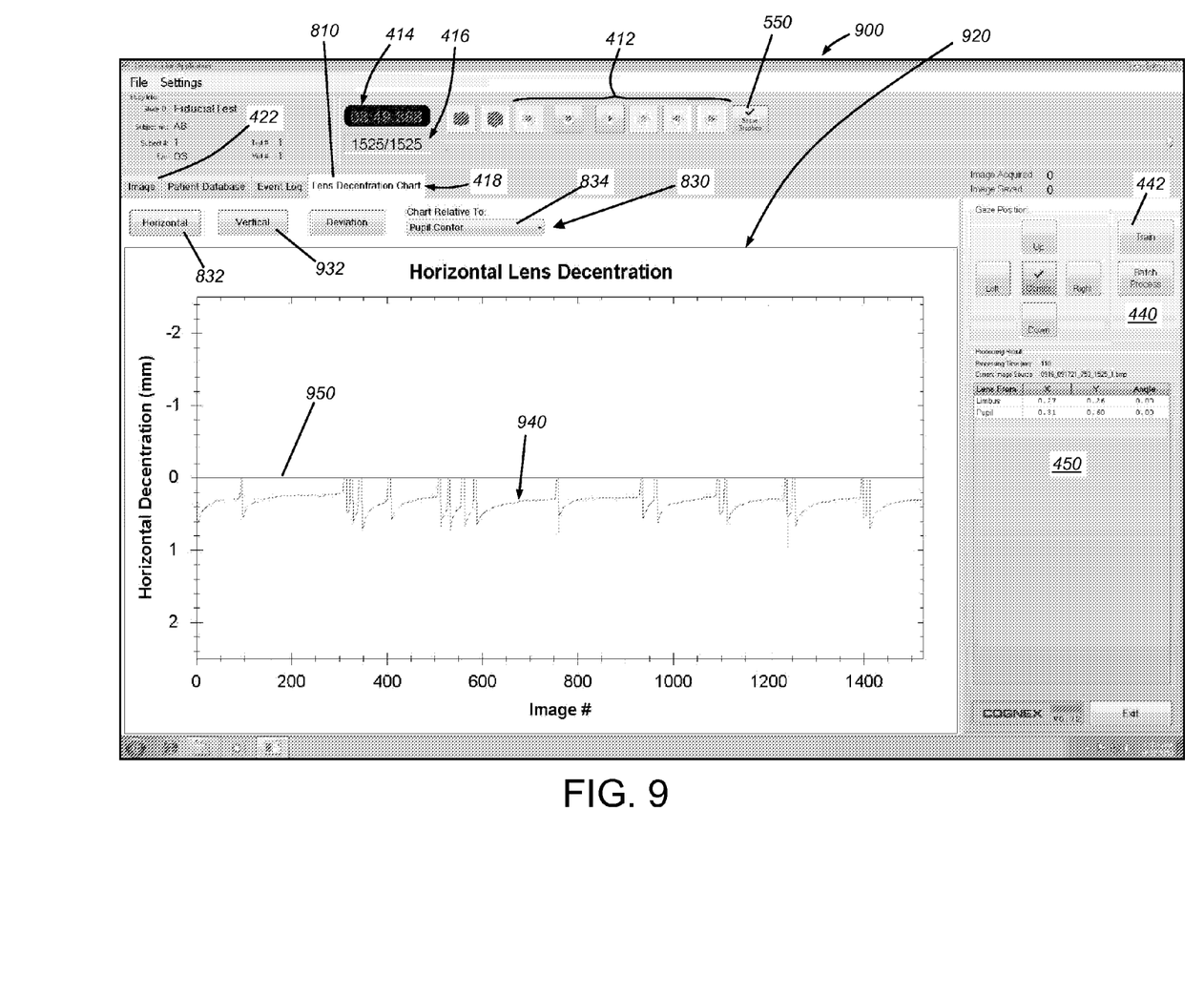
FIG. 9 is a diagram of the graphical user interface display of FIG. 4 showing a generated graph of a lens horizontal decentration (horizontal component of movement from the centered position on the eye) based upon a predetermined number of successive images.

FIG. 9, likewise, depicts a display 900 in which a graph 920 shows horizontal lens decentration (plot 940) versus the pupil center (line 950) for each image frame in the file. Spikes in the plot represent blinks.

Figure 10:
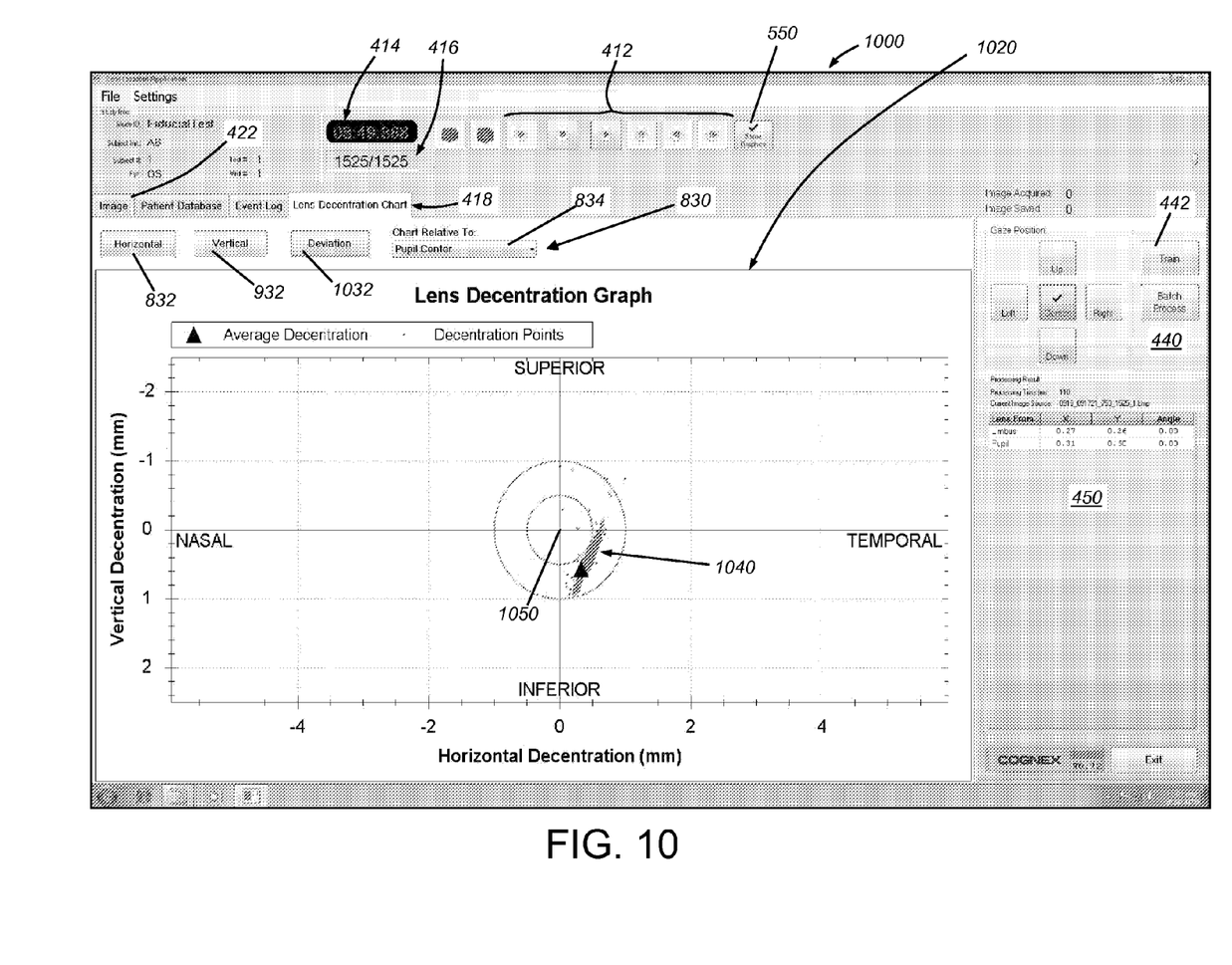
FIG. 10 is a two-dimensional decentration graph showing a scatter plot of lens center points with respect to the eye's (pupil and/or limbus) center point.

FIG. 10 depicts a display 1000 in which the vertical and horizontal decentration versus pupil center are plotted in a graph 1020. The average decentration appears as a swarm of data points relative to the pupil center 1050. This plot is generated by activating the deviation button 1032.

It should be clear that a variety of other formats (graphs, images, graphical overlays, etc.) can be employed for displaying and analyzing data in accordance with alternate embodiments.

Figure 11:
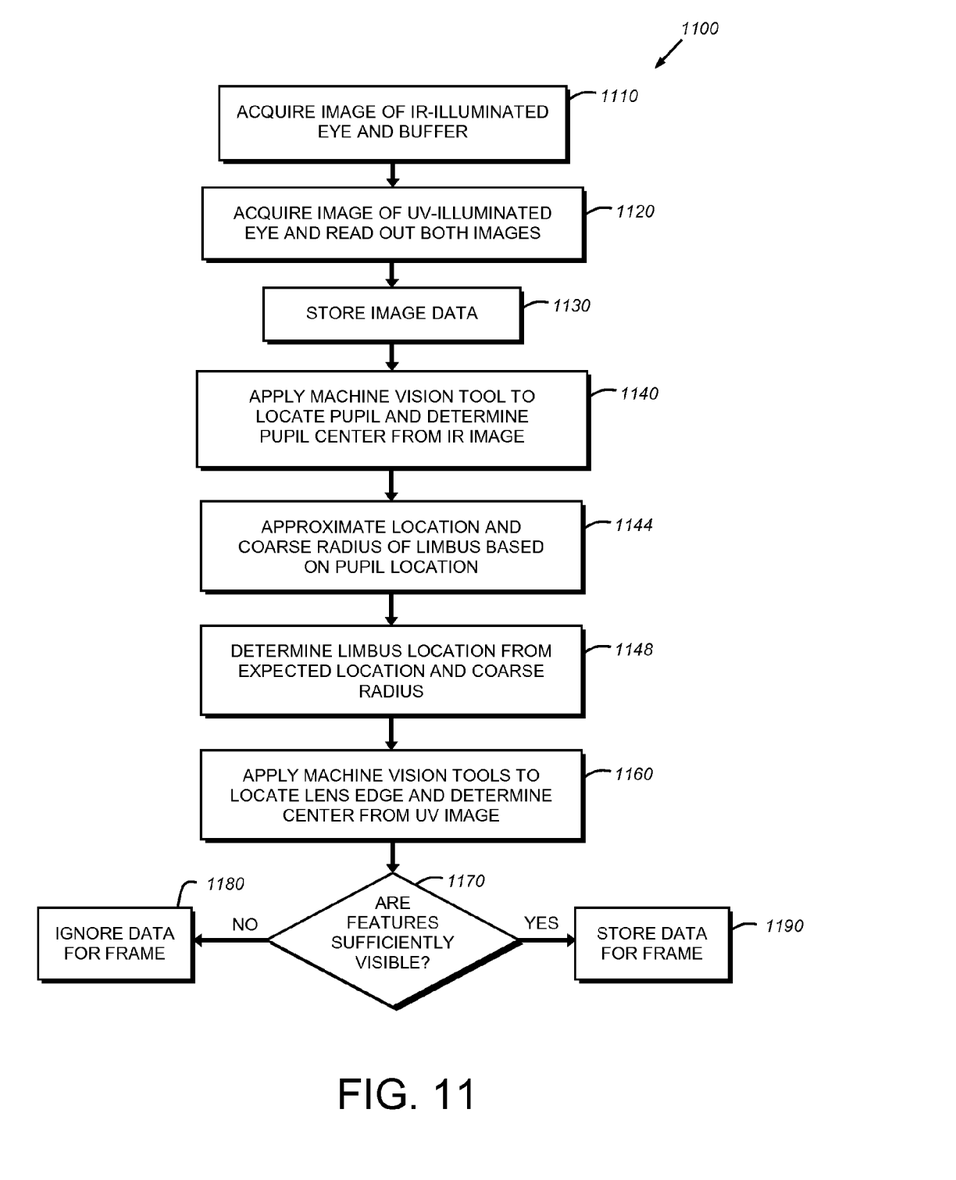
FIG. 11 is a flow diagram of a runtime procedure for automated determination and generation of contact lens position and movement data with respect to the subject wearer's eye according to an illustrative embodiment.

The process 1100 for determining the positions of the pupil, limbus and contact lens is now described in further detail with reference to FIG. 11. The process can be carried out frame-by frame, or by retrieving previously acquired raw image data from storage after acquisition of a video clip of associated frames. An image frame of the eye with contact lens is acquired by the sensor using IR illumination (as described generally above) in step 1110, and the charge is buffered. The sensor then acquires an image frame of the eye using UV illumination in step 1120. As defined herein, the IR and UV images in a given pair of frames are acquired a directs succession—meaning that either image in the pair is acquired closely enough in time that there is little or no significant movement of the eye between frames in the pair that could render the analysis inaccurate. As defined the direct succession can be either UV first followed by IR, or vice versa. In this embodiment, the rapidity between frames is achieved by buffering charge in the pixel array while a new acquisition occurs. In alternate embodiments, other techniques can be used to achieve directly-subsequent acquisition.

Both acquired images in the frame pair are read out to digital storage (as grayscale pixel values), which can be an online memory and/or a storage file on, for example, a hard disk (step 1130). Note that the order in which UV and IR images are acquired and stored can be reversed in alternate embodiments. A machine vision tool is applied to the raw IR image data in step 1140. This tool can comprise one or more RSIS vision tools, such as the above-described Patmax™ application. These tools accommodate any skew in the eye due to an offset gaze or camera axis that is not normal to the eye. The tools locate the pupil based upon a trained pattern, and thereby determine a center thereof. A circle can be fit to the pupil, including a circle radius. These values are stored for the IR image frame.

Having determined the location of the pupil, the approximate location of the limbus is now determined. This is based in part upon an assumption that the center of the limbus is somewhat near the center of the pupil (although typically slightly offset). An approximation of the limbus radius (coarse radius) is thereby made, emanating from the pupil center. Based upon the coarse radius and center, the refined location of the limbus is the determined in step 1148. In an embodiment, this entails defining an annular region around the pupil center, having therewithin the coarse radius. The annular region is then subjected to a polar unwrap process in which the annulus is translated into a rectangle, using radial and polar coordinates in a rectilinear plot. This results in an approximate line across the plot where the iris meets the sclera (i.e. a translation of the approximately circular limbus). Illustratively, a caliper (edge) tool is employed to determine the line's location, and this value is translated into a fitted circle and center for the limbus.

Next, the contact lens location is determined using machine vision tools in step 1160. In an embodiment, an RSIS tool such as Patmax™ can be employed to find the coarse location of the circle defined by the lens, and this is then refined by a circle fitting tool. This tool determined the center of the circle, thereby providing the lens location. This location can be compared to both the pupil location and the limbus location using the techniques described above.

In a further decision step 1170, which can occur after the frames are analyzed, or earlier in the overall process 1100, the system and method determines whether sufficient exposed edge for the lens, limbus and/or pupil is present. When a wearer blinks some or all of the edge becomes occluded. If insufficient portions of an edge are exposed, then the analysis indicates a blink is occurring and omits the computed data (step 1180). Conversely, if sufficient edge is present, then the data for the frame is stored in a data file for subsequent analysis. As described above, the data can be stored in a variety of forms, including a comma-separated file of circles and centers relative to the pupil, limbus and lens in each frame.

In an optional step, the machine vision tools can apply a mask that is used to remove specular reflections from various portions of the image during analysis, where information is unlikely to exist, such as the inner pupil and sclera. This speeds processing and reduces potential errors where otherwise false edges can exist.

While the described camera implements a process in which two discrete, directly succeeding images are acquired, it is expressly contemplated that a single illumination event, in which both IR and UV pixel data are acquired substantially simultaneously can be implemented in an alternate embodiment. Such an embodiment a combination of IR and UV illumination is triggered simultaneously in a single strobe, and the camera is constructed and arranged as a multi-spectral camera that images IR and UV simultaneously. Such a camera can be constructed analogously to RBG cameras which use, for example, a single sensor that includes a Bayer filter or multiple sensors that each receive transmitted light via a prism (not shown). In this implementation some of the sensor's pixels selectively receive IR light and some pixels receive UV light during the discrete, combined IR (or visible) and UV strobe event. In such embodiments, the delay between capture of the UV and IR images is essentially zero. The image data from IR pixels and UV pixels is read-out simultaneously, and analyzed in accordance with the general procedures described above.

It should be clear that a wide variety of vision system techniques and processes can be employed to determine the location of the pupil and limbus in alternate embodiments. It should also be clear that the system and method described above provides an effective and robust solution to tracking the position of a contact lens on a wearer's eye without the need of fiducials or the use of uncomfortable visible illumination light. The data generated by the system and method can also be displayed and manipulated in a variety of useful ways that assist both developers and medical practitioners in analyzing the performance of a particular contact lens with respect to a user.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, in alternate embodiments, the system and method can determine and store data with respect to the pupil only or limbus only in providing a reference to the eye relative to lens position. In other embodiments, the pupil center and eye center can be used to approximate an additional center point that is used as a reference. Also, where a particular vision system tool is described, a plurality of discrete tools can also be included to carry out the function of the particular tool. Moreover, the any of the processes and procedures employed herein can be implemented using hardware, software consisting of a computer-readable medium of program instructions, or a combination of hardware and software. Accordingly, this description is meant to be taken only by way of example, and not to otherwise limit the scope of this invention.

What is claimed is:

1. A system for tracking position and movement of a contact lens on a wearer's eye comprising:
    a camera constructed and arranged to acquire a first image of the eye using a first illumination and a second image of the eye using a second illumination, allowing viewing of a pupil and a limbus of the eye;
    at least one vision system tool constructed and arranged to:
        a) determine a location of the pupil and a location of the limbus in the second image; and
        b) determine a location of the contact lens in the first image; and
    a graphical user interface that displays a visible image of the eye and includes overlay graphics showing the location of the contact lens and the location of the pupil and the limbus with respect to the contact lens.

2. The system as set forth in claim 1 wherein the first illumination is UV light.

3. The system as set forth in claim 2 wherein the second illumination is IR light.

4. The system as set forth in claim 1 further comprising a graphical user interface that displays a graph showing the location of the contact lens with respect to the location of a reference point.

5. The system as set forth in claim 4 wherein the reference point is at least one of the location of the pupil and the location of the limbus.

6. The system as set forth in claim 1 wherein the first image is acquired at a first time and the second image is acquired at a second time, wherein the first image and the second image occur in an order wherein one of the first time and the second time in a direct succession with respect to other of the first time and the second time.

7. The system of claim 1 wherein the first illumination causes the contact lens to appear opaque with respect to the surrounding eye and the second illumination causes the contact lens to appear transparent with respect to the surrounding eye.

8. A method for tracking position and movement of a contact lens on a wearer's eye comprising the steps of:
    acquiring a first image of the eye using a first illumination and a second image of the eye using a second illumination, allowing viewing of a pupil and a limbus of the eye;
    determining a location of the pupil and a location of the limbus in the second image; and
    determining a location of the contact lens in the first image;
    displaying a visible image of the eye on a graphical user interface and including overlay graphics showing the location of the contact lens and the location of the pupil and the limbus with respect to the contact lens.

9. The method as set forth in claim 8 wherein the first image is acquired at a first time and the second image is acquired at a second time, wherein the first image and the second image occur in an order wherein one of the first time and the second time in a direct succession with respect to other of the first time and the second time.

10. The method of claim 8 wherein the first illumination is UV light.

11. The method of claim 8 wherein the second illumination is IR light.

12. The method of claim 8 further comprising a graphical user interface that displays a graph showing the location of the contact lens with respect to the location of a reference point.

13. The method of claim 12 wherein the reference point is at least one of the location of the pupil and the location of the limbus.

14. The system of claim 8 wherein the first illumination causes the contact lens to appear opaque with respect to the surrounding eye and the second illumination causes the contact lens to appear transparent with respect to the surrounding eye.

* * * * *